United States Patent [19]

Luscombe et al.

[11] Patent Number: 5,258,012
[45] Date of Patent: Nov. 2, 1993

[54] SURGICAL FASTENERS

[75] Inventors: Brian H. Luscombe, Somerset, N.J.; David A. Witt, Loveland; Kirk M. Nicola, Cincinnati, both of Ohio

[73] Assignee: Ethicon, Inc., Somerville, N.J.

[21] Appl. No.: 906,606

[22] Filed: Jun. 30, 1992

[51] Int. Cl.5 .............................................. A61B 17/00
[52] U.S. Cl. ...................................... 606/220; 227/902
[58] Field of Search .................. 606/219, 220; 227/902

[56] References Cited

U.S. PATENT DOCUMENTS

| | | | |
|---|---|---|---|
| 4,060,089 | 11/1977 | Noiles | 128/325 |
| 4,402,445 | 9/1983 | Green | 227/19 |
| 4,506,670 | 3/1985 | Crossley | 128/334 R |
| 4,506,671 | 3/1985 | Green | 128/334 R |
| 4,513,746 | 4/1985 | Aranyl et al. | 128/334 C |
| 4,534,352 | 8/1985 | Korthoff | 128/334 C |
| 4,589,416 | 5/1986 | Green | 128/334 C |
| 4,610,250 | 9/1986 | Green | 128/334 C |
| 4,667,674 | 5/1987 | Korthoff et al. | 128/334 C |
| 4,724,839 | 2/1988 | Bedi et al. | 128/334 C |
| 4,805,617 | 2/1989 | Bedi et al. | 128/334 C |
| 4,917,114 | 4/1990 | Green et al. | 227/179 |
| 4,932,960 | 6/1990 | Green et al. | 606/220 |
| 4,994,073 | 2/1991 | Green | 606/220 |
| 5,089,009 | 2/1992 | Green | 606/219 |

Primary Examiner—Stephen C. Pellegrino
Assistant Examiner—Gary Jackson
Attorney, Agent, or Firm—Paul A. Coletti; Charles P. Boukus

[57] ABSTRACT

A two-part surgical fastener comprises a staple and a receiver which are adapted to secure body tissue together. The staple is generally U-shaped and includes at least two prongs with barbed distal ends which penetrate the tissue and are latched by the receiver. Each prong of the staple is configured as an elongated prism of hexagonal cross-section and includes a barbed tip with an enlarged hexagonal cross-section at its free end. Each aperture of the receiver is hexagonal in configuration and includes a pair of opposed ledges for engaging the barbed tip. The tip of each prong has a pointed distal end formed by a first pair of sloped surfaces which form the sharp angle and a second pair of sloped surfaces which form a blunt angle. The staple includes longitudinal ridges or grooves on the prongs which are engaged and guided by longitudinal channels or ribs provided in a staple cartridge. The staple and receiver consist of bioabsorbable material.

33 Claims, 7 Drawing Sheets

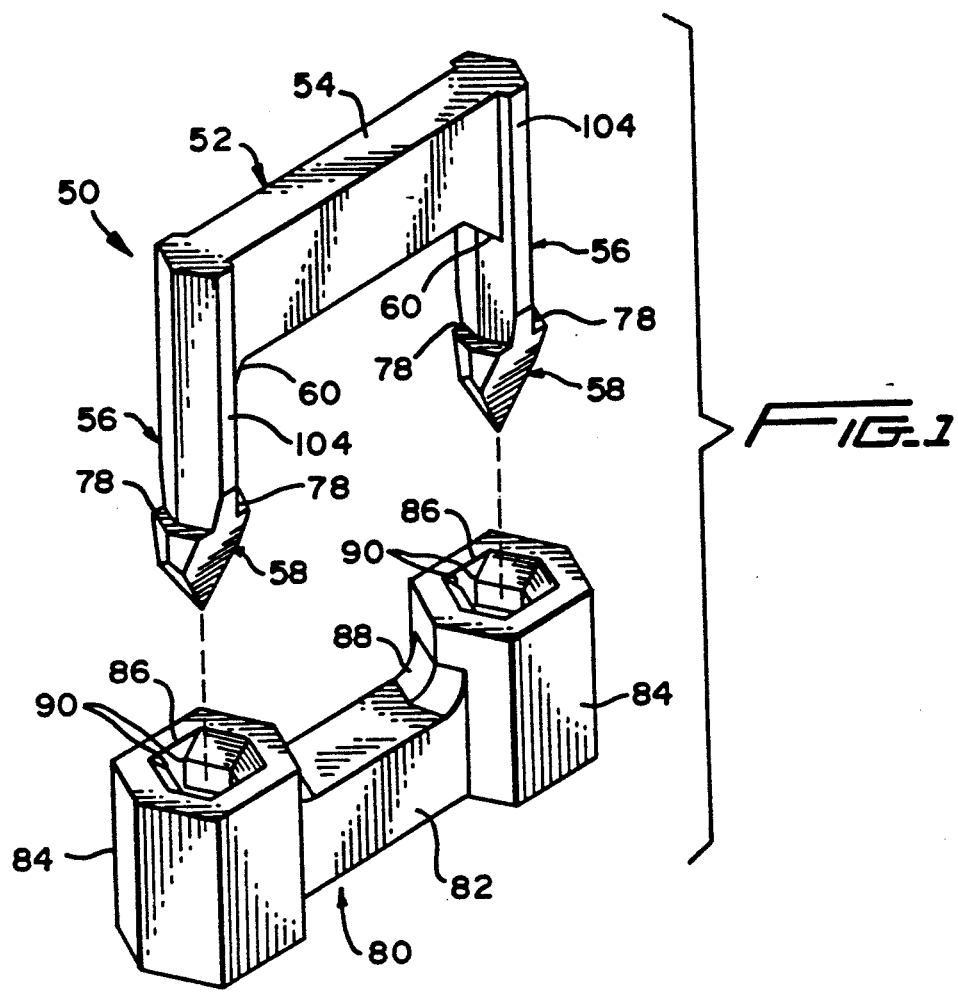
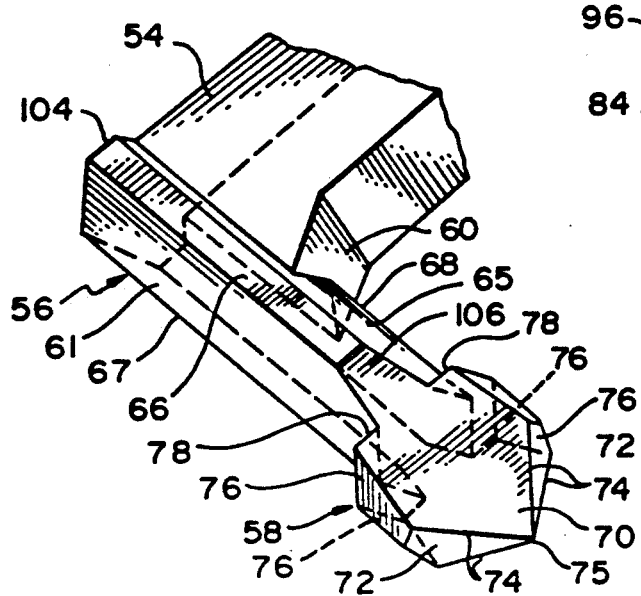

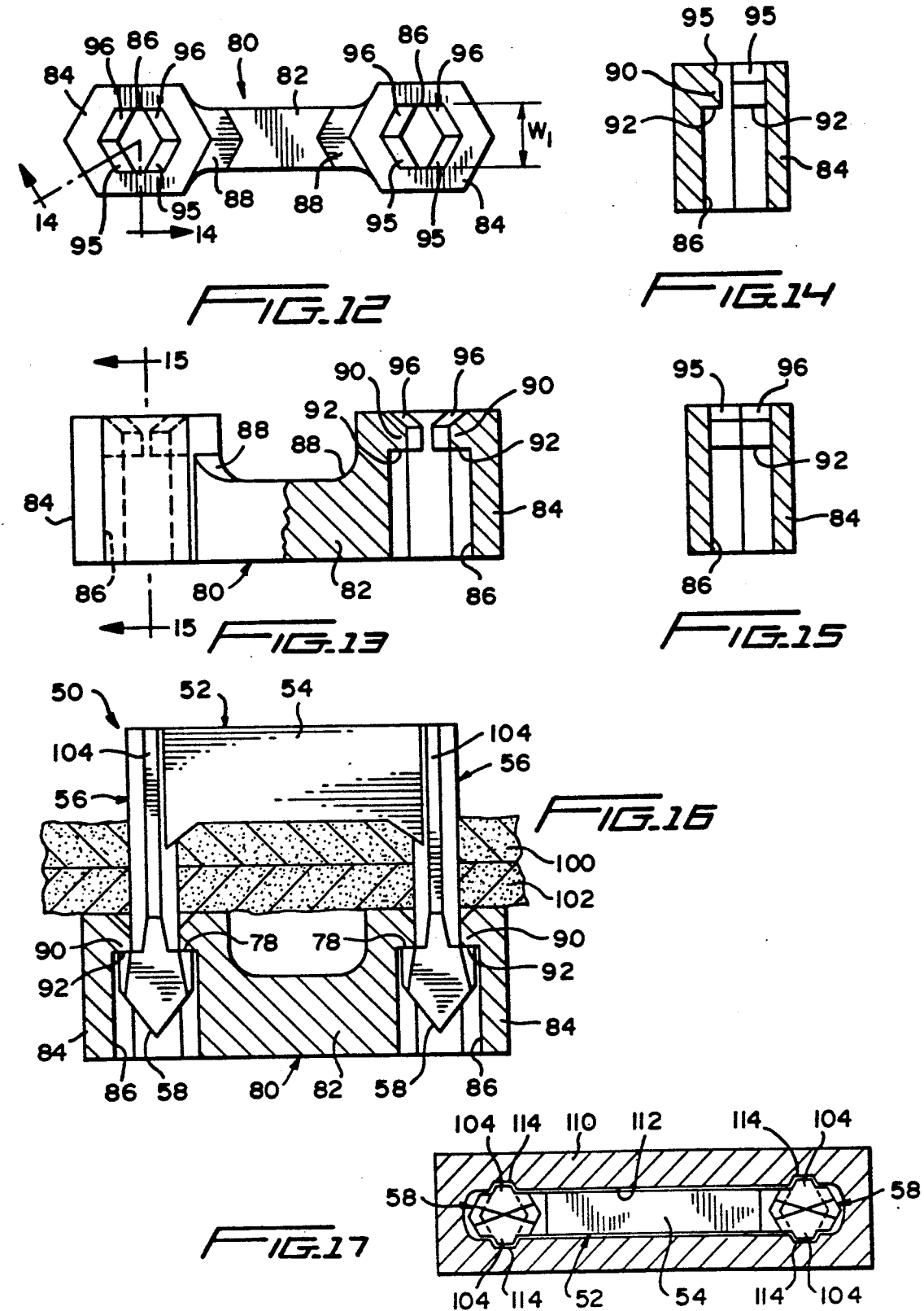

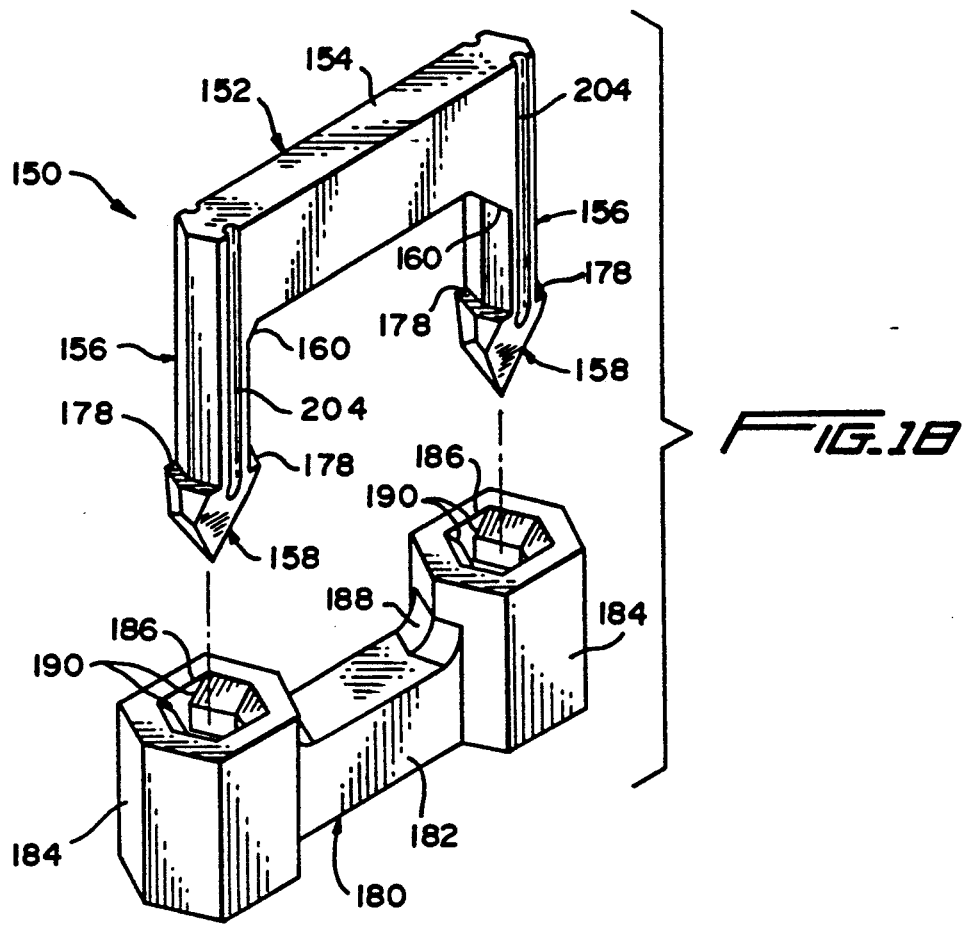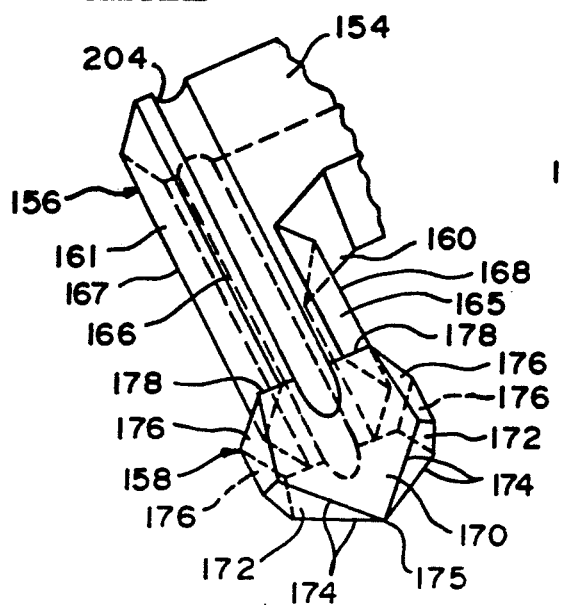

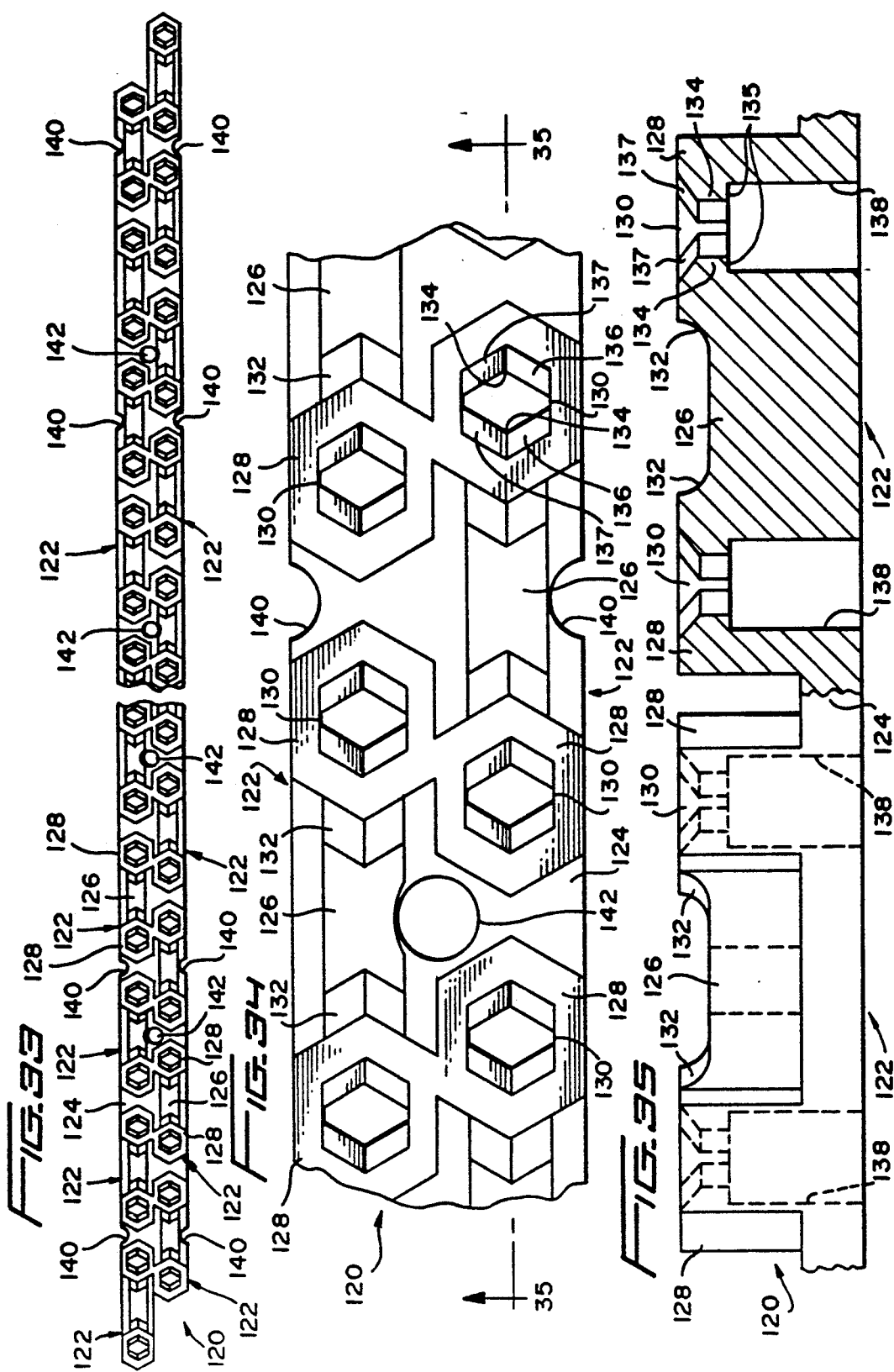

SURGICAL FASTENERS

DESCRIPTION

Field of the Invention

The present invention relates to surgical fasteners and, more particularly, to a two-part surgical fastener of bioabsorbable material which comprises a staple and a receiver to fasten and/or compress body tissue together for hemostasis.

BACKGROUND OF THE INVENTION

Surgical fasteners, or staples, are commonly used in surgical procedures to allow a surgeon to fasten body tissue together without the need for time consuming suturing procedures. The surgical fasteners can be applied to the body tissue by using surgical staplers which operate to install the fasteners one at a time or to apply a plurality of fasteners in succession or simultaneously. The staplers typically include fastener cartridges from which the fasteners are driven into the tissue.

Two-part surgical fastener devices are previously known. Such devices include a fastener member, or staple, which is generally U-shaped in configuration with a pair of prongs, and a retainer member provided with apertures in which the prongs are engaged and latched. The fastener prongs pierce the body tissue from one side and the retainer member latches the prongs on the other side of the tissue. The surgical fasteners, once engaged, are not separable so that, after being inserted into the body tissue, the fasteners cannot be easily removed. Accordingly, two-part surgical fasteners consist of bioabsorbable material which is absorbed into the body tissue.

U.S. Pat. No. 4,060,089 (Noiles) discloses a fastener strip with multiple barbed prongs and a retainer strip with a plurality of longitudinally spaced openings for receiving the prongs.

U.S. Pat. No. 4,402,445 (Green) discloses a two-pronged fastener with a retainer piece.

U.S. Pat. No. 4,506,670 (Crossley) discloses a two-part surgical fastener in which the retainer piece is held to a supporting member by a lug with a frangible member. The prongs of the fastener, upon entering the apertures of the retainer, break the frangible members and push out the lugs, thereby releasing the retainer piece from the supporting member.

U.S. Pat. No. 4,506,671 (Green) discloses the same two-part surgical fastener disclosed in Crossley U.S. Pat. No. 4,506,670.

U.S. Pat. No. 4,513,746 (Aranyi et al) discloses a two-piece surgical fastener in which the fastener portion has two prongs with outer channels for receiving a tissue piercing member. The retainer piece has extensions with apertures for receiving the prongs of the fastener and longitudinally extending expansion slots.

U.S. Pat. No. 4,534,352 (Korthoff) discloses a two-part surgical fastener including a fastener member with prongs having an increased surface area to volume ratio for faster absorption. Various prong cross-sections are disclosed including round, square, cruciform, channel-shaped and a plurality of fins.

U.S. Pat. No. 4,589,416 (Green) discloses a surgical fastener retainer member assembly including a plurality of retainer members linked together in various configurations including straight and circular rows.

U.S. Pat. No. 4,610,250 (Green) discloses a two-part surgical fastener including a fastener member with four prongs which mate with four openings in the retainer member. The two inner prongs are bent toward each other by camming surfaces in the corresponding openings in the retainer member.

U.S. Pat. No. 4,667,674 (Korthoff et al) discloses a two-part surgical fastener including an extended base to improve hemostasis.

U.S. Pat. No. 4,724,839 (Bedi et al) discloses a surgical fastening system including a staple with two legs of circular cross section. Each leg has a tapered, pointed tip with opposed flange portions extending only partially around the circumference of the leg.

U.S. Pat. No. 4,805,617 (Bedi et al) discloses a surgical fastening system including a plurality of receivers arranged in at least two parallel rows and interconnected by a continuous thin layer or web consisting of the plastic material of which the receivers are formed.

U.S. Pat. No. 4,917,114 (Green et al) discloses a two-part surgical fastener which is annular in configuration.

U.S. Pat. No. 4,932,960 (Green et al) discloses a two-part absorbable surgical fastener including fins on the lateral and transverse sides of the prongs for extra strength. The columns of the retainer member have lateral expansion slots.

U.S. Pat. No. 4,994,073 (Green) discloses a skin fastener in which each prong has a triangularly shaped barb which is flat on both sides to minimize body tissue resistance. The fastener includes indentations which align the fastener with rail members inside an ejection chamber of a surgical stapling apparatus.

U.S. Pat. No. 5,089,009 (Green) discloses an inwardly biased skin fastener including two barbed prongs.

In the use of two-part surgical fasteners, there is a tendency for the fastener prongs to buckle as the fastener is driven through the tissue and inserted into the retainer. As a result of the axial forces encountered, the fastener prongs may buckle outwardly in opposite directions relative to each other, or inwardly toward each other. It is also possible that the fastener prongs may tend to buckle in the same direction under axial loads. This tendency of the fastener prongs to buckle has the undesired effect of increasing the force which must be exerted on the fastener to penetrate the tissue and insert the prongs into the retainer. Also, the prongs may become misaligned with the apertures in the retainer thereby increasing the difficulty of inserting the fastener prongs into the retainer. To avoid these drawbacks, it is desirable to provide a fastener structure with prongs of sufficient strength to resist buckling to facilitate the penetration of the tissue by the fastener prongs and to facilitate the insertion of the fastener prongs into the retainer. Also, it is desirable to provide a fastener with prongs of sufficient strength to sustain the axial loads encountered when the fastener and retainer are assembled to hold the tissue together.

In surgery, it is often desirable to place multiple rows of fasteners in stitching procedures. Two side by side rows of fasteners aligned end to end along the lengthwise direction of the fastener, for example, will exhibit greater holding power and hemostasis than a single row of fasteners. To facilitate the placement of multiple rows, it is desirable to have a staple which is as narrow as possible, particularly if the staple is to be applied endoscopically. However, if the fastener is made narrower for a particular length and shape, the fastener prongs become relatively weaker due to the reduced amount of structural material present in the prongs.

Accordingly, it is desirable to provide a surgical fastener which is sufficiently narrow to be inserted endoscopically and installed in multiple rows of fasteners without compromising the strength of the fastener prongs.

It is also advantageous to provide a surgical fastener in which the prongs have pointed tips which facilitate the penetration of the fastener prongs into the body tissue and the insertion of the prongs into the retainer. To minimize the penetration force, it is desirable to provide the tip with an arrowhead-like shape which tends to spread the tissue apart rather than to cut through the tissue. Also, it is desirable to design the tip to achieve self-alignment with the apertures in the retainer and to provide uniform latching when the fastener and the retainer are assembled.

Furthermore, a fastener which is adapted to be supported and guided in a fastener cartridge can avoid the problems associated with the misalignment of the fastener prongs with the apertures in the retainer when the prongs are inserted through the tissue into the retainer. Thus, it is desirable to design the fastener prongs to be engaged and guided for movement in the staple cartridge.

SUMMARY OF THE INVENTION

Accordingly, it is an object of the present invention to provide an improved two-part surgical fastener with enhanced fastening strength and buckling resistance.

It is also an object of the invention to provide a surgical fastener with a sharp tip for tissue penetration without compromising the strength of the prongs.

Another object of the invention is to provide a two-part surgical fastener which is suitable for internal use to fasten and compress layers of body tissue together for hemostasis or to compress a single layer of body tissue for hemostasis.

It is another object of the invention to provide a surgical fastener or staple with prongs which are structurally adapted to engage a set of guideways for movement along a staple cartridge.

These and further objects and advantages are achieved herein by providing a surgical fastener comprising a fastener member including a base and at least two spaced substantially parallel prongs extending substantially perpendicularly from the base, a receiver member including at least two apertures, each aperture being adapted to receive and retain the free end of a respective one of the prongs, and each prong being configured as an elongated prism with a hexagonal cross-section. Each prong of the fastener member has a barbed tip with a hexagonal cross-section at its free end. The tip has a larger hexagonal cross-section than the prong to provide a pair of barbs located on opposite sides of the prong. Each aperture of the receiver member is hexagonal in configuration for receiving one of the prongs and tips of the fastener. Each aperture includes a pair of opposed ledges for engaging the barbs to retain the tip in the aperture.

In accordance with another aspect of the invention, each tip of the fastener member has a pointed distal end formed by a first pair of sloped surfaces which form a sharp angle and a second pair of sloped surfaces which form a blunt angle. In a preferred embodiment, the sharp angle is in the range of 20-60 degrees and the blunt angle is at least 25 degrees more than the sharp angle.

In accordance with another feature of the invention, the fastener member includes guide means on the prongs which is adapted to engage a fastener cartridge to guide the fastener member in movement relative to the cartridge. A first embodiment of the fastener member includes one or more ridges extending longitudinally along the prongs for engaging guide channels provided in the fastener cartridge. A second embodiment of the fastener member includes one or more grooves extending longitudinally along the prongs which are engaged and guided by longitudinal ribs provided in the fastener cartridge.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a perspective view of a first embodiment of a surgical fastener device including a staple and a receiver constructed in accordance with the invention;

FIG. 2 is an enlarged perspective view of one of the prongs of the staple of FIG. 1;

FIG. 3 is an enlarged perspective view of one of the columns of the receiver of FIG. 1;

FIG. 12 is a top view of the receiver of FIG. 1;

FIG. 13 is a front elevation, partially in section, of the receiver of FIG. 1;

FIG. 14 is a vertical section along line 14—14 of FIG. 12;

FIG. 15 is a vertical section along line 15—15 of FIG. 13;

FIG. 16 is a front elevation, partially in section, showing the staple and receiver of FIG. 1 fastened together;

FIG. 17 is a section view showing the staple of FIG. 1 mounted in a staple cartridge;

FIG. 18 is a perspective view of a second embodiment of a surgical fastener device including a staple and a receiver constructed in accordance with the invention;

FIG. 19 is an enlarged perspective view of one of the prongs of the staple of FIG. 18;

FIG. 20 is an enlarged perspective view of one of the columns of the receiver of FIG. 18;

FIG. 33 is a plan view of a receiver strip including two rows of receivers;

FIG. 34 is an enlarged plan view of a portion of the receiver strip of FIG. 33; and FIG. 35 is a longitudinal section of the receiver strip along line 35—35 of FIG. 34.

DETAILED DESCRIPTION OF PREFERRED EMBODIMENTS

Figure 4:
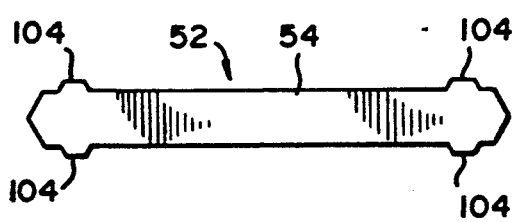
FIG. 4 is a top view of the staple of FIG. 1.

The present invention provides a two-part surgical fastener comprising a staple and a receiver which are adapted to secure and/or to compress body tissue together. The staple is generally U-shaped and includes at least two prongs with barbed distal ends which penetrate the tissue and are latched by the receiver. The function of the surgical fastener is to compress the body tissue together for hemostasis and to maintain the compression for a desired period of time. The surgical fastener can be used to secure and compress two layers of body tissue together or to compress a single layer of body tissue, e.g., to close off a blood vessel or a vascular region of tissue. The staple and receiver consist of bioabsorbable material to eliminate the need to remove the surgical fastener from the body.

Referring to FIG. 1, in a first embodiment of the invention, a surgical fastener, generally 50, comprises a U-shaped staple or fastener 52 including an elongated, generally rectangular base 54 with at least two spaced substantially parallel prongs 56 extending substantially perpendicularly from the base 54. Preferably, the prongs 56 are located at the opposite ends of the base 54. Each prong 56 includes a barbed tip 58 at its distal end. A sloped buttress 60 is formed at each end of the base 54 for reinforcement of the prongs 56.

Figure 8:
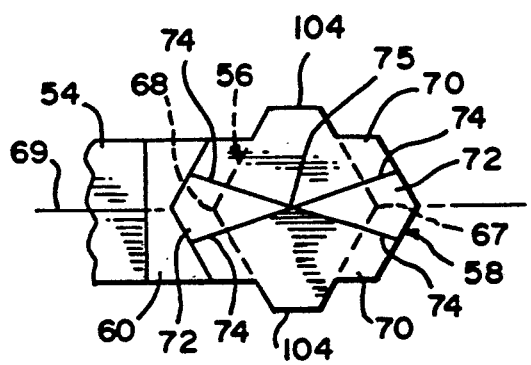
FIG. 8 is an enlarged bottom view of one prong of the staple of FIG. 1.
Figure 9:
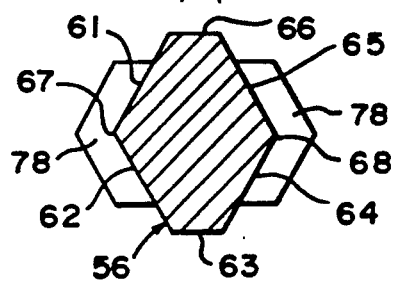
FIG. 9 is a horizontal section of one prong of the staple taken along line 9—9 of FIG. 5.
Figure 10:
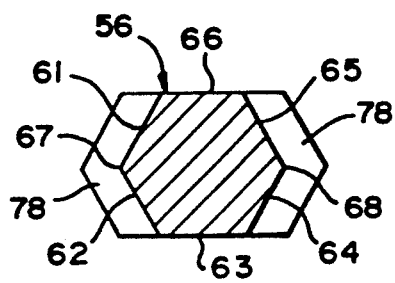
FIG. 10 illustrates another hexagonal cross-section for the prongs of the staple of FIG. 1.
Figure 11:
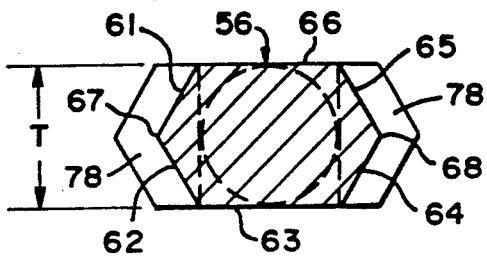
FIG. 11 illustrates another hexagonal cross-section for the prongs of the staple of FIG. 1.
Figure 21:
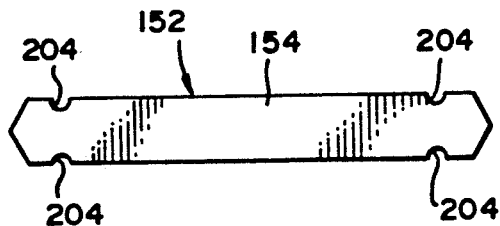
FIG. 21 is a top view of the staple of FIG. 18.

As shown in FIGS. 2 and 9, each prong 56 is configured in the shape of an elongated hexagonal prism. The prong 56 has a hexagonal cross-section with six sides 61–66 (FIG. 9) which are elongated and substantially rectangular in shape. The sides 61 and 62 intersect each other along an outer vertical edge 67 of the prong 56 and the sides 64 and 65 intersect each other along an inner vertical edge 68 of the prong 56. The outer edge 67 and the inner edge 68 of each prong 56 are aligned in the same plane as the centerline 69 (FIG. 8) of the base 54. Preferably, the internal angles of the hexagonal cross-section are all approximately 120 degrees. The sides 61–66 of the hexagonal cross-section may be equal in length or may vary in length depending on the hexagonal shape desired for the prongs 56. FIG. 9 shows a hexagonal cross-section of the prong 56 in which the sides 61, 62, 64 and 65 are equal in length and longer than the opposite sides 63 and 66 of the hexagonal cross-section. FIG. 10 shows a prong 56 with a cross-section in the form of a regular hexagon in which the sides 61–66 are equal in length and the internal angles are each 120 degrees. FIG. 11 shows a prong 56 with a hexagonal cross-section in which the opposite sides 63 and 66 are longer than the sides 61, 62, 64 and 65. A prong 56 with the hexagonal cross-section of FIG. 11 provides an increased buckling strength compared with a similar prong of circular or square cross-section of the same thickness T.

Figure 5:
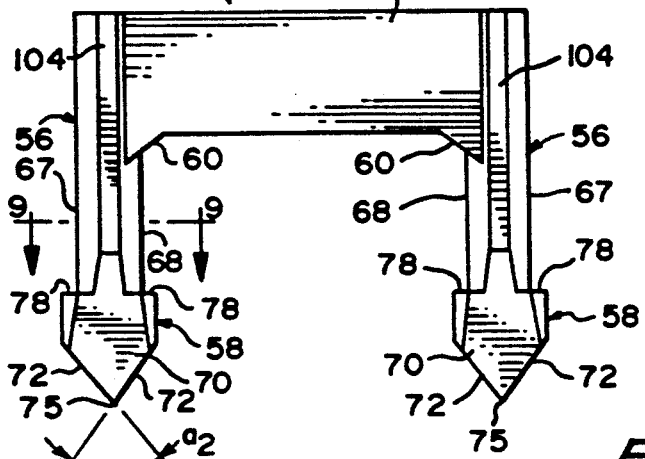
FIG. 5 is a front elevation of the staple of FIG. 1.
Figure 7:
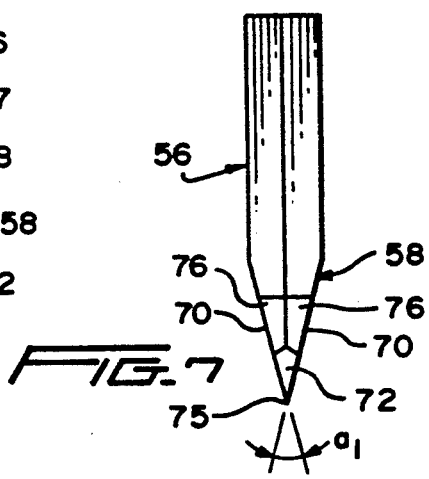
FIG. 7 is a side view of the staple of FIG. 1.

Referring to FIG. 2, the tip 58 of each prong 56 has an arrowhead-like shape to facilitate tissue penetration. Generally, each tip 58 is formed as an additional hexagonal prism with a larger cross-sectional area than the hexagonal prism which forms the prong 56. The arrowhead-like shape of the tip 58 is achieved by a first pair of sloped surfaces 70 (FIG. 7) along opposite faces of the tip 58 which form a relatively sharp angle a1 and a second pair of sloped surfaces 72 (FIG. 5) on opposite sides of the tip 58 which form a more obtuse or blunt angle a2. Preferably, the sharp angle a1 is in the range of about 20–60 degrees and the blunt angle a2 is at least 25 degrees more than the angle a1. As shown in FIGS. 2 and 8, the sloped surfaces 70 and 72 intersect each other along a set of four piercing edges 74 which meet at a pointed distal end 75 of the tip 58. If desired, additional sloped surfaces (not shown), which intersect the sloped surfaces 70 and 72, may be provided to form the pointed distal end 75 of the tip 58.

Referring to FIG. 2, the tip 58 has a multi-faceted configuration including the first pair of sloped surfaces 70 and the second pair of sloped surfaces 72. Two pairs of facets 76 are formed by the hexagonal sides of the head 58. Because the tip 58 has a larger hexagonal cross-section than the prong 56, the tip 58 has a pair of ledges or barbs 78 which are positioned on opposite sides of the prong 56 and face in the proximal direction toward the base 54. As shown in FIG. 9, the outer ledge or barb 78 extends along the adjacent sides 61 and 62 of the hexagonal cross-section of the prong 56 and the inner ledge or barb 78 extends along the adjacent sides 64 and 65 of the hexagonal cross-section of the prong 56.

The effect of sloping the surfaces 70 and 72 at different angles is to provide a tip 58 which tends to spread the tissue, like an arrowhead, rather than to cut the tissue when the staple 52 is installed. This action reduces the force required for the staple 52 to penetrate the tissue. Also, by locating the surfaces 72 which form the blunt angle a2 along opposite edges of the tip 58, the ledges or barbs 78 have a greater surface area than if the blunt angle a2 is formed between the sloped surfaces 70 on the opposite faces of tip 58.

Referring to FIG. 1, the surgical fastener 50 also comprises a retainer 80 which is adapted to receive and retain the distal ends of the prongs 56. As shown in FIGS. 12 and 13, the retainer 80 includes an elongated bridge 82 connected at its opposite ends to a pair of columns 84 provided with apertures 86 for receiving the prongs 56 and the barbed tips 58 of the staple 52. The bridge 82 is provided with rounded buttresses 88 at its opposite ends which reinforce the apertured columns 84. The bridge 82 (FIG. 13) is reduced in height relative to the apertured columns 84. However, if desired, the bridge 82 and the columns 84 can be made of the same height.

As shown in FIGS. 1 and 3, when viewed from the top, each column 84 has an external hexagonal configuration. The tip receiving apertures 86 are also hexagonal in configuration. At the top of each aperture 86, a pair of opposed ledges 90 extends inwardly from the inner side walls of the aperture 86. Each ledge 90 has an overhang 92 (FIG. 13) facing in the distal direction for engaging the ledge or barb 78 on the tip 58 when the prong 56 is inserted into the aperture 86. As shown in FIG. 12, each ledge 90 includes front and rear portions 93 and 94 which extend along adjacent sides of the hexagonal aperture 86. The front and rear ledge portions 93 and 94 have top chamfered surfaces 95 and 96, respectively, which are sloped downwardly and inwardly to guide the multi-faceted tip 58 into the apertures 86 and facilitate the alignment of the staple 52 in the receiver 80.

Referring to FIG. 16, the surgical fastener 50 is shown in its assembled configuration to fasten two pieces of body tissue 100 and 102 together. The pieces of tissue 100 and 102 are pierced by the prongs 56 and the barbed tips 58 which extend into the apertures 86 in the receiver 80. The prongs 56 are latched in the apertures 86 by the underhangs 92 on the ledges 90 which engage the barbs 78 on the tips 58. The pieces of tissue 100 and 102 are clamped together between the base 54 of the staple 52 and the bridge 82 and columns 84 of the receiver 80.

To facilitate the installation of the surgical fastener 50, the receiver 80 is made of elastic material which is more flexible than the material of the staple 52. Preferably, the receiver 80 consists of flexible, resilient material which is elastically deformable to enable the prongs 56 and the barbed tips 58 to be pushed through the spaces between the ledges 90 in each aperture 86. After the prongs 56 are inserted into the apertures 86, the resilient material of the ledges 90 returns to its undeformed condition to latch the barbed tips 58. The staple 52 consists of relatively rigid material, compared with the material of the receiver 80, to facilitate the penetration of the tissue by the staple prongs 56. For example, the receiver 80 can be made of a bioabsorbable polymer or plastic material such as polydioxanone (known as PDS TM, a trademark of Ethicon, Inc.) and the staple 52 can be made of a blend of lactide/glycolide copolymer and polyglycolic acid (PGA).

Figure 6:
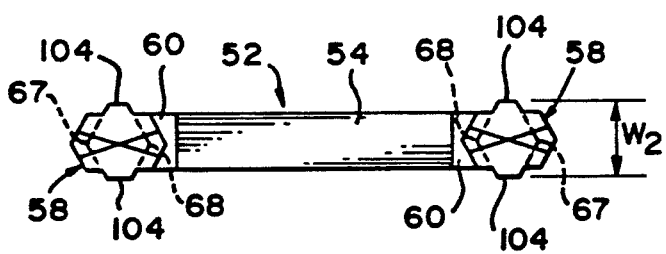
FIG. 6 is a bottom view of the staple of FIG. 1.

Referring to FIGS. 6 and 12, each aperture 86 has a width W1 which is slightly greater than the width W2 of the prong 56. This difference in widths allows the receiver 80 to deform more readily during the insertion of the staple 52 and reduces the insertion force (compared with more conventional staples and receivers) required to insert the staple 52 into the receiver 80.

In the embodiment of FIGS. 1-9, the prongs 56 include staple guide means in the form of a pair of elongated ridges 104 extending longitudinally along the opposite faces of each prong 56. As shown in FIG. 9, the staple guiding ridges 104 are formed by extending the sides 61, 62, 64 and 65 outwardly so that the sides 63 and 66 of the prong 56 project laterally outward beyond the base 54 of the staple 52. As shown in FIG. 2, the sloped surfaces 70 on each tip 58 provide a pair of sloped ramps 106 at the front of the elongated ridges 104 on each prong 56.

Referring to FIG. 17, a staple cartridge 110 includes at least one staple slot or channel 112 for slidably receiving a staple 52. A staple driver (not shown) is mounted in the channel 112 for driving the staple 52 from the staple cartridge 110 into the body tissue. The staple cartridge 110 includes a set of four longitudinal grooves 114 which are arranged in opposed pairs for receiving the elongated ridges 104 on the prongs 56 of the staple 52. The longitudinal grooves 114 provide guideways which receive the elongated ribs 104 and guide the staple 52 in longitudinal movement along the channel 112 of the cartridge 110. The grooves 114 also support the staple 52 in the cartridge 110 so that the effective buckling length of the staple 52 is reduced thereby optimizing its buckling strength.

Referring to FIG. 18, in a second embodiment of the invention, a surgical fastener, generally 150, comprises a U-shaped staple or fastener 152 including an elongated, generally rectangular base 154 with at least two spaced substantially parallel prongs 156 extending substantially perpendicularly from the base 154. Preferably, the prongs 156 are located at the opposite ends of the base 154. Each prong 156 includes a barbed tip 158 at its distal end. A sloped buttress 160 is formed at each end of the base 154 for reinforcement of the prong 156.

Figure 25:
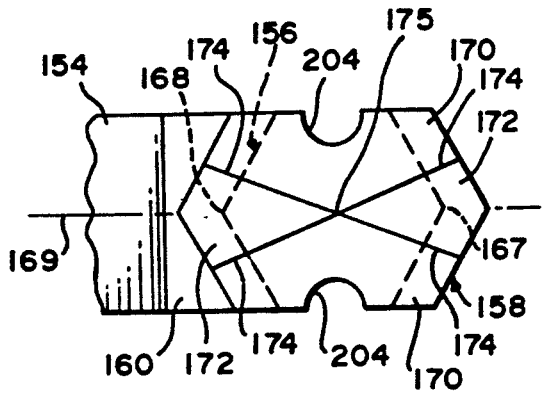
FIG. 25 is an enlarged bottom view of one prong of the staple of FIG. 18.
Figure 22:
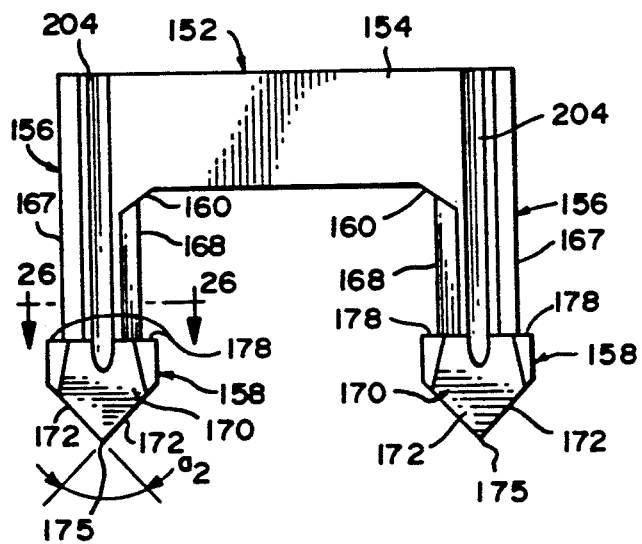
FIG. 22 is a front elevation of the staple of FIG. 18.
Figure 26:
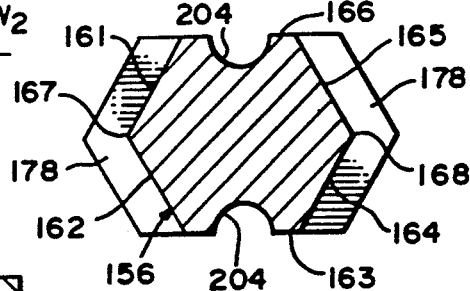
FIG. 26 is a horizontal section of one prong of the staple taken along line 26—26 of FIG. 22.

As shown in FIG. 19, each prong 156 is configured in the shape of an elongated hexagonal prism. The prong 156 has a hexagonal cross-section with six sides 161-166 (FIG. 26) which are elongated and substantially rectangular in shape. The sides 161 and 162 intersect each other along an outer vertical edge 167 of the prong 156 and the sides 164 and 165 intersect each other along an inner vertical edge 168 of the prong 156. The outer edge 167 and the inner edge 168 of each prong 156 are aligned in the same plane as the centerline 169 (FIG. 25) of the base 154. Preferably, the internal angles of the hexagonal cross-section are all approximately 120 degrees. The sides 161-166 of the hexagonal cross-section may be equal in length or may vary in length depending on the hexagonal shape desired for the prongs 156. FIG. 26 shows a prong 156 with a cross-section in the form of a regular hexagon in which the sides 161-166 are equal in length and the internal angles are each 120 degrees.

Figure 24:
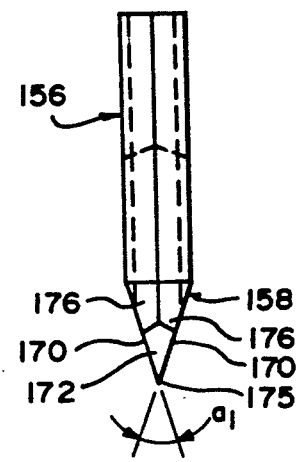
FIG. 24 is a side view of the staple of FIG. 18.

Referring to FIG. 19, the tip 158 of each prong 156 has an arrowhead-like shape to facilitate tissue penetration. Generally, each tip 158 is formed as an additional hexagonal prism with a larger cross-sectional area than the hexagonal prism which forms the prong 156. The arrowhead-like shape of the tip 158 is achieved by a first pair of sloped surfaces 170 (FIG. 24) along opposite faces of the tip 158 which form a relatively sharp angle a1 and a second pair of sloped surfaces 172 (FIG. 5) on opposite sides of the tip 158 which form a more obtuse or blunt angle a2. Preferably, the sharp angle a1 is in the range of about 20-60 degrees and the blunt angle a2 is at least 25 degrees more than the angle a1. As shown in FIGS. 19 and 25, the sloped surfaces 170 and 172 intersect each other along a set of four piercing edges 174 which meet at a pointed distal end 175 of the tip 158. If desired, additional sloped surfaces (not shown), which intersect the sloped surfaces 170 and 172, may be provided to form the pointed distal end 175 of the tip 158.

Referring to FIG. 19, the tip 158 has a multi-faceted configuration including the first pair of sloped surfaces 170 and the second pair of sloped surfaces 172. Two pairs of facets 176 are formed by the hexagonal sides of the head 158. Because the tip 158 has a larger hexagonal cross-section than the prong 156, the tip 158 has a pair of ledges or barbs 178 which are positioned on opposite sides of the prong 156 and face in the proximal direction toward the base 154. As shown in FIG. 26, the inner ledge or barb 178 extends along the adjacent sides 161 and 162 of the hexagonal cross-section of the prong 156 and the outer ledge or barb 178 extends along the adjacent sides 164 and 165 of the hexagonal cross-section of the prong 156.

The effect of sloping the surfaces 170 and 172 at different angles is to provide a tip 158 which tends to spread the tissue, like an arrowhead, rather than to cut the tissue when the staple 152 is installed. This action reduces the force required for the staple 152 to penetrate the tissue. Also, by locating the surfaces 172 which form the blunt angle a2 along opposite edges of the tip 158, the ledges or barbs 178 have a greater surface area than if the blunt angle a2 is formed between the sloped surfaces 170 on the opposite faces of tip 158.

Figure 28:
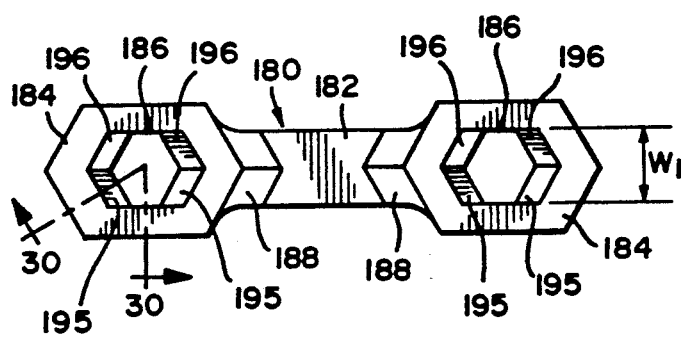
FIG. 28 is a top view of the receiver of FIG. 18.
Figure 30:
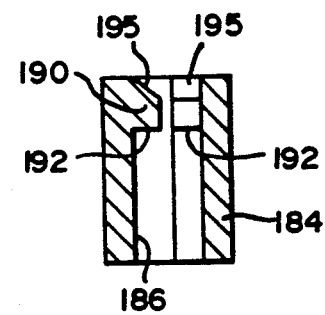
FIG. 30 is a vertical section along line 30—30 of FIG. 28.
Figure 29:
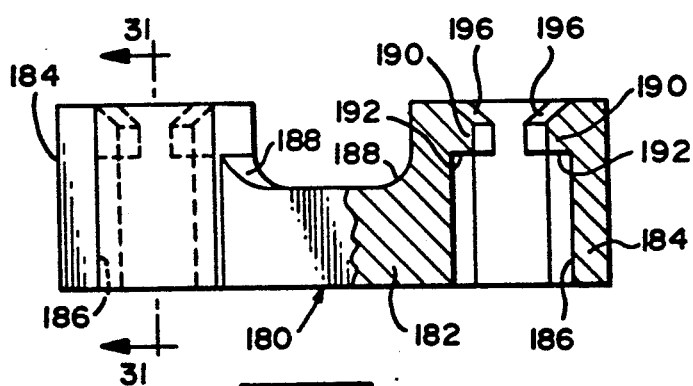
FIG. 29 is a front elevation, partially in section, of the receiver of FIG. 18.
Figure 31:
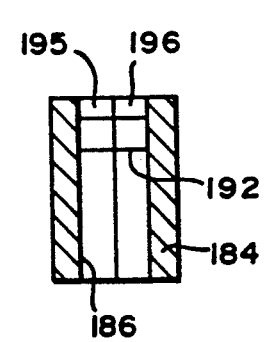
FIG. 31 is a vertical section along line 31—31 of FIG. 29.

Referring to FIG. 18, the surgical fastener 150 also comprises a retainer 180 which is adapted to receive and retain the distal ends of the prongs 156. As shown in FIGS. 28 and 29, the retainer 180 includes an elongated bridge 182 connected at its opposite ends to a pair of columns 184 provided with apertures 186 for receiving the prongs 156 and the barbed tips 158 of the staple 152. The bridge 182 is provided with rounded buttresses 188 at its opposite ends which reinforce the apertured columns 184. The bridge 182 (FIG. 29) is reduced in height relative to the apertured columns 184. However, if desired, the bridge 182 and the columns 184 can be made of the same height.

As shown in FIGS. 18 and 20, when viewed from the top, each column 184 has an external hexagonal configuration. The tip receiving apertures 186 are also hexagonal in configuration. At the top of each aperture 186, a pair of opposed ledges 190 extends inwardly from the inner side walls of the aperture 186. Each ledge 190 has an overhang 192 (FIG. 29) facing in the distal direction for engaging the ledge or barb 178 on the tip 158 when the prong 156 is inserted into the aperture 186. As shown in FIG. 28, each ledge 190 includes front and rear portions 193 and 194 which extend along adjacent sides of the hexagonal aperture 186. The front and rear ledge portions 193 and 194 have top chamfered surfaces 195 and 196, respectively, which are sloped downwardly and inwardly to guide the multi-faceted tip 158 into the apertures 186 and facilitate the alignment of the staple 152 in the receiver 180.

To facilitate the installation of the surgical fastener 150, the receiver 180 is made of elastic material which is more flexible than the material of the staple 152. Preferably, the receiver 180 consists of flexible, resilient material which is elastically deformable to enable the prongs 156 and the barbed tips 158 to be pushed through the spaces between the ledges 190 in each aperture 186. After the prongs 156 are inserted into the apertures 186, the resilient material of the ledges 190 returns to its undeformed condition to latch the barbed tips 158. The staple 152 consists of relatively rigid material, compared with the material of the receiver 180, to facilitate the penetration of the tissue by the staple prongs 156. For example, the receiver 180 can be made of a bioabsorbable polymer or plastic material such as polydioxanone (known as PDS TM, a trademark of Ethicon, Inc.) and the staple 152 can be made of a blend of lactide/-glycolide copolymer and polyglycolic acid (PGA).

Figure 23:
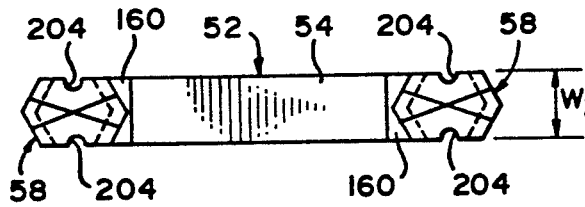
FIG. 23 is a bottom view of the staple of FIG. 18.
Figure 32:
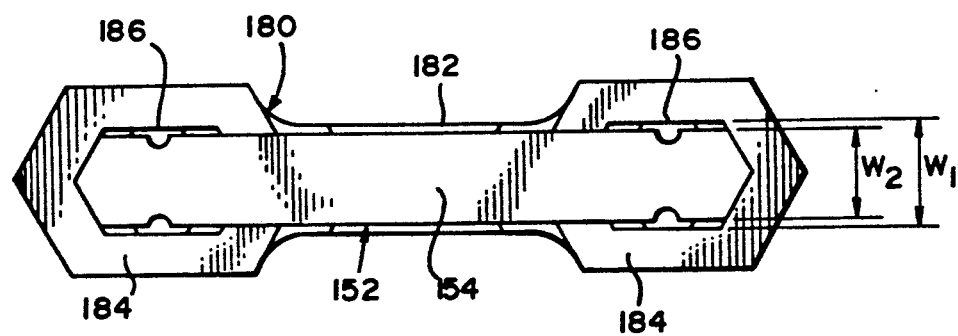
FIG. 32 is an enlarged top view showing the staple and receiver of FIG. 18 fastened together.

Referring to FIGS. 23 and 28, each aperture 186 has a width W1 which is slightly greater than the width W2 of the prong 156. As shown in FIG. 32, this difference in widths allows the receiver 180 to deform more readily during the insertion of the staple 152 and reduces the insertion force (compared with more conventional staples and receivers) required to insert the staple 152 into the receiver 180.

In the embodiment of FIGS. 18–26, the prongs 156 include staple guide means formed as a pair of elongated grooves 204 extending longitudinally along the opposite faces of each prong 156. As shown in FIG. 26, the staple guiding grooves 204 are formed as semi-circular indentations in the opposite sides 163 and 166 of the prong 156. Also, other configurations can be used for the grooves 204 such as V-shaped and U-shaped indentations.

Figure 27:
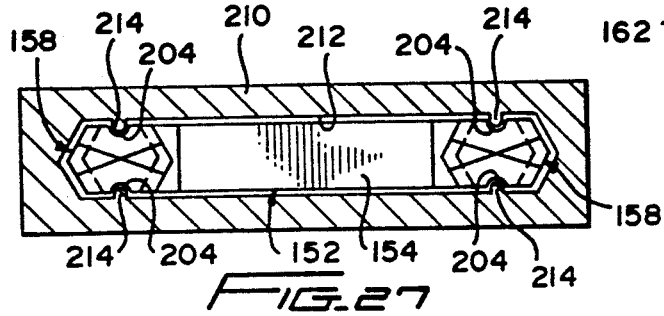
FIG. 27 is a section view showing the staple of FIG. 18 mounted in a staple cartridge.

Referring to FIG. 27, a staple cartridge 210 includes at least one staple slot or channel 212 for slidably receiving a staple 152. A staple driver (not shown) is mounted in the channel 212 for driving the staple 152 from the staple cartridge 210 into the body tissue. The staple cartridge 210 includes a set of four longitudinal ribs 214 which are arranged in opposed pairs and are received in the elongated grooves 204 on the prongs 156 of the staple 152. The longitudinal ribs 214 provide guideways which engage the elongated grooves 204 and guide the staple 152 in longitudinal movement along the channel 212 of the cartridge 210. The ribs 214 also support the staple 152 in the cartridge 210 so that the effective buckling length of the staple 152 is reduced thereby optimizing its buckling strength.

Referring to FIG. 33, an elongated receiver strip 120 includes a plurality of receiver units 122 connected together by a webbing 124. The receiver strip 120 is manufactured as a single molded piece of bioabsorbable material. Each receiver unit 122 is similar in construction to the receiver 80 of FIG. 1 and is adapted to receive and retain one staple 52. The receiver units 122 are arranged, for example, in two staggered rows with twelve receiver units 122 in each row.

As shown in FIGS. 34 and 35, each receiver unit 122 includes an elongated bridge 126 connected at its opposite ends to a pair of columns 128 provided with apertures 130 for receiving the prongs 56 and the barbed tips 58 of the staple 52. Each bridge 126 is provided with rounded buttresses 132 at its opposite ends which reinforce the apertured columns 128. The webbing 124 is reduced in thickness compared with the bridge 126 and the columns 128 of each receiver unit 122.

As shown in FIG. 34, when viewed from the top, each column 128 has a generally hexagonal external configuration. The tip receiving apertures 130 are also hexagonal in configuration. At the top of each aperture 130, a pair of opposed ledges 134 extends inwardly from the inner side walls of the aperture 130. Each ledge 134 has an overhang 135 (FIG. 35) facing in the distal direction for engaging the ledge or barb 78 on the staple tip 58 when the prong 56 is inserted into the aperture 130. As shown in FIG. 34, each ledge 134 includes front and rear portions 136 and 137 which extend along adjacent sides of the hexagonal aperture 130. The front and rear ledge portions 136 and 137 are sloped downwardly and inwardly to guide the multi-faceted staple tip 58 into the apertures 130 and facilitate the alignment of the staple 52 with the receiver unit 122. Each aperture 130 includes a circular counterbore 138 which extends upwardly from the bottom of the strip 120 and terminates at the underhangs 135 of the ledges 134 for receiving the staple tip 58.

As shown in FIG. 33, the receiver strip 120 includes a plurality of notches 140 spaced apart along the opposite edges of the webbing 124. The notches 140 receive a set of alignment ribs (not shown) provided in a receiver cartridge of a surgical stapler to align the receiver strip 120 in the cartridge. Alternatively, the receiver strip 120 has a plurality of through holes 142 formed in the webbing 124 for receiving a set of alignment pins (not shown) provided in a receiver cartridge to align the receiver strip 120 in the cartridge.

The receiver strip 120 is applied with a plurality of staples 52 of the type shown in FIG. 1 to fasten body tissue together. The prongs 56 of the staples 54 are driven through the tissue and inserted into the apertures 130 of the receiver strip 120. The barbs 78 on the tips 58 are engaged by the underhangs 135 on the ledges 134 to latch the staples 54 to the receiver strip 120.

The receiver strip 120 includes two staggered rows of receiver units 122 for receiving a series of staples 152 which are arranged in overlapping adjacent rows for hemostasis. However, it will be understood that, if desired, the receiver strip 120 can be made with a single row of receiver units 122. Also, the receiver units 122 can be arranged in a circular pattern on the receiver strip 120 for use in fastening tubular pieces of tissue together.

The invention in its broader aspects is not limited to the specific details of the preferred embodiments shown and described, and those skilled in the art will recognize that the invention can be practiced with modification within the spirit and scope of the appended claims.

We claim:

1. A surgical fastener, comprising:
   a fastener member including a base and at least two spaced substantially parallel prongs extending substantially perpendicularly from said base;
   a receiver member including at least two apertures, each aperture being adapted to receive and retain the free end of a respective one of the prongs; and
   each prong being configured as an elongated prism with a hexagonal cross section.

2. The surgical fastener of claim 1, wherein:
   each prong has a barbed tip with a hexagonal cross section at its free end.

3. The surgical fastener of claim 2, wherein said receiver member includes:
   means for engaging and retaining said barbed tips of said prongs in said apertures.

4. The surgical fastener of claim 2, wherein:
   said tip has a larger hexagonal cross section than said prong to provide a pair of barbs located on opposite sides of said prong.

5. The surgical fastener of claim 4, wherein:
   each aperture is hexagonal in configuration for receiving one of said prongs and tips.

6. The surgical fastener of claim 5, wherein:
   each aperture includes a pair of opposed ledges for engaging said barbs to retain said tip in said aperture.

7. The surgical fastener of claim 4, wherein:
   each tip has a pointed distal end formed by a first pair of sloped surfaces which form a sharp angle and a second pair of sloped surfaces which form a blunt angle.

8. The surgical fastener of claim 7, wherein:
   said sharp angle is in the range of 20-60 degrees and said blunt angle is at least 25 degrees more than said sharp angle.

9. The surgical fastener of claim 7, wherein said fastener member includes:
   guide means on said prongs adapted to engage a fastener cartridge to guide said fastener member in movement relative to said cartridge.

10. The surgical fastener of claim 9, wherein said guide means comprises:
    at least one ridge extending longitudinally along said prongs.

11. The surgical fastener of claim 9, wherein said guide means comprises:
    at least one groove extending longitudinally along said prongs.

12. The surgical fastener of claim 1, wherein said fastener member and said receiver consist of bioabsorbable material.

13. The surgical fastener of claim 1, wherein:
    said receiver member consists of material which is more flexible than the material of said staple.

14. The surgical fastener of claim 13, wherein:
    said apertures in said receiver member are wider than said prongs of said fastener member.

15. A surgical fastener, comprising:
    a fastener member including a base and at least two spaced substantially parallel prongs extending substantially perpendicularly from said base; and
    each prong being configured as an elongated prism with a hexagonal cross section.

16. The surgical fastener of claim 15, wherein:
    each prong has a barbed tip with a hexagonal cross section at its free end.

17. The surgical fastener of claim 16, wherein:
    said tip has a larger hexagonal cross section than said prong to provide a pair of barbs located on opposite sides of said prong.

18. The surgical fastener of claim 15, wherein:
    each tip has a pointed end formed by a first pair of sloped surfaces which form a sharp angle and a second pair of sloped surfaces which form a blunt angle.

19. The surgical fastener of claim 18, wherein:
    said sharp angle is in the range of 20-60 degrees and said blunt angle is at least 25 degrees more than said sharp angle.

20. The surgical fastener of claim 15, which includes:
    guide means on said prongs adapted to engage a fastener cartridge to guide said fastener member in movement relative to said cartridge.

21. The surgical fastener of claim 20, wherein said guide means comprises:
    at least one ridge extending longitudinally along said prongs.

22. The surgical fastener of claim 20, wherein said guide means comprises:
    one or more grooves extending longitudinally along said prongs.

23. The surgical fastener of claim 15, wherein said fastener member consists of bioabsorbable material.

24. A surgical fastener, comprising:
    a fastener member including a base and at least two spaced substantially parallel prongs extending substantially perpendicularly from said base; and
    each prong having a tip with a pointed end formed by a first pair of sloped surfaces which form a sharp angle and a second pair of sloped surfaces which form a blunt angle and wherein said sharp angle is in the range of 20-60 degrees and said blunt angle is at least 25 degrees more than said sharp angle.

25. The surgical fastener of claim 24, wherein:
    said tip having an enlarged cross sectional area to provide a pair of barbs on opposite sides of said prong.

26. The surgical fastener of claim 24, which includes:
    guide means on said prongs adapted to engage a fastener cartridge to guide said fastener member in movement relative to said cartridge.

27. The surgical fastener of claim 26, wherein said guide means comprises:
    at least one ridge extending longitudinally along said prongs.

28. The surgical fastener of claim 26, wherein said guide means comprises:

at least one groove extending longitudinally along said prongs.

29. The surgical fastener of claim 24, wherein said fastener member consists of bioabsorbable material.

30. A receiver assembly for use with a plurality of surgical fastener members to fasten body tissue together, each fastener member having at least two spaced substantially parallel prongs of hexagonal cross section, said receiver assembly comprising:

a plurality of surgical fastener receiver units arranged in one or more rows, each of said receiver units including at least two spaced hexagonal apertures adapted to receive and retain the prongs of one surgical fastener member; and said surgical fastener receiver units being connected together by a webbing extending between the adjacent receiver members in each row.

31. The receiver assembly of claim 30, which includes:

alignment means on said webbing for aligning said receiver assembly with a receiver cartridge.

32. The receiver assembly of claim 30, wherein said alignment means comprises:

a plurality of notches spaced apart along the opposite edges of said webbing.

33. The receiver assembly of claim 30, wherein said alignment means comprises:

a plurality of through holes spaced apart in said webbing.

* * * * *